United States Patent [19]

Herrmann et al.

[11] Patent Number: 5,037,987
[45] Date of Patent: Aug. 6, 1991

[54] PRODUCTION OF OPTICAL ISOMERS OF CERTAIN 1,6-NAPHTHYRIDINE-3-CARBOXYLATE DERIVATIVES

[75] Inventors: Wolfgang Herrmann, Merzhausen; Jürgen Kleinschroth, Denzlingen; Klaus Steiner, Waldkirch, all of Fed. Rep. of Germany

[73] Assignee: Goedecke Aktiengesellschaft, Berlin, Fed. Rep. of Germany

[21] Appl. No.: 486,048

[22] Filed: Feb. 27, 1990

[30] Foreign Application Priority Data

Mar. 1, 1989 [DE] Fed. Rep. of Germany ....... 3906460

[51] Int. Cl.$^5$ ........................................... C07D 471/04
[52] U.S. Cl. ..................................................... 546/123
[58] Field of Search ........................................ 546/123

[56] References Cited

U.S. PATENT DOCUMENTS 3,832,388 8/1984 Lorenz ................................. 562/444
4,711,901 12/1987 Satzinger et al. .................... 546/123
4,751,228 6/1988 Kleinschroth et al. ............. 546/123
4,760,081 7/1988 Satzinger et al. .................... 546/123

Primary Examiner—Bernard Dentz
Attorney, Agent, or Firm—Elizabeth M. Anderson

[57] ABSTRACT

The present invention provides a process for the separation of the naphthyridine derivatives (±)-1,4-dihydro-5-isopropoxy-2-methyl-4-(2-trifluoromethylphenyl)-1,6-naphthyridine-3-carboxylic acid ethyl ester and (±)-1,4-dihydro-5-isopropoxy-2-methyl-4-(2-trifluoromethylphenyl)-1,6-naphthyridine-3-carboxylic acid [2-(N-methyl-N-phenylmethylamino)ethyl] ester into the optical antipodes by use of the (±)-1,4-dihydro-5-isopropoxy-2-methyl-4-(2-trifluoromethylphenyl)-1,6-naphthyridine-3-carboxylic acid benzyl ester and optically-active O,O'-dibenzoyltartaric acid. Said optical antipodes are calcium antagonists useful in the treatment of blood vessel diseases.

1 Claim, No Drawings

PRODUCTION OF OPTICAL ISOMERS OF CERTAIN 1,6-NAPHTHYRIDINE-3-CARBOXYLATE DERIVATIVES

BACKGROUND OF THE INVENTION

The naphthyridine derivatives (±)-1,4-dihydro-5-isopropoxy-2-methyl-4-(2-trifluoromethylphenyl)-1,6-naphthyridine-3-carboxylic acid ethyl ester

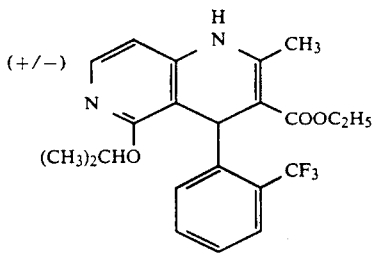

and (±)-1,4-dihydro-5-isopropoxy-2-methyl-4-(2-trifluoromethylphenyl)-1,6-naphthyridine-3-carboxylic acid [2-(N-methyl-N-phenylmethylamino)-ethyl]ester

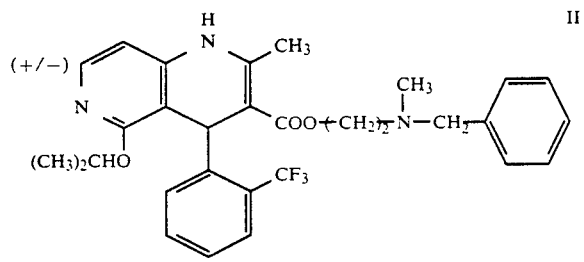

are covered in Germany Patent Number 34 31 303 as highly effective calcium antagonists. U.S. Pat. Nos. 4,711,901, 4,760,081, and 4,751,228 are the corresponding patents and are incorporated herein by reference.

SUMMARY OF THE INVENTION

The instant invention concerns novel compounds:
(+)-1,4-dihydro-5-isopropoxy-2-methyl-4-(2-trifluoromethylphenyl)-1,6-naphthyridine-3-carboxylic acid ethyl ester,
(−)-1,4-dihydro-5-isopropoxy-2-methyl-4-(2-trifluoromethylphenyl)-1,6-naphthyridine-3-carboxylic acid ethyl ester,
(+)-1,4-dihydro-5-isopropoxy-2-methyl-4-(2-trifluoromethylphenyl)-1,6-naphthyridine-3-carboxylic acid,
(−)-1,4-dihydro-5-isopropoxy-2-methyl-4-(2-trifluoromethylphenyl)-1,6-naphthyridine-3-carboxylic acid,
(+)-1,4-dihydro-5-isopropoxy-2-methyl-4-(2-trifluoromethylphenyl)-1,6-naphthyridine-3-carboxylic acid[2-(N-methyl-N-phenylmethylamino)ethyl]ester, and
(−)-1,4-dihydro-5-isopropoxy-2-methyl-4-(2-trifluoromethylphenyl)-1,6-naphthyridine-3-carboxylic acid[2-(N-methyl-N-phenylmethylamino)ethyl]ester.

The instant invention also concerns novel processes for making the above compounds. The process comprises
(a) reacting (±)-1,4-dihydro-5-isopropoxy-2-methyl-4-(2-trifluoromethylphenyl)-1,6-naphthyridine-3-carboxylic acid ethyl ester with benzyl alcohol to produce the corresponding (±) benzyl ester,
(b) reacting the (±) benzyl ester from step (a) with (+) or (−) dibenzoyltartaric acid followed by fractional distillation to produce the desired (+) or (−) salt,
(c) hydrogenating the (+) or (−) salt from step (b) to produce the corresponding (+) or (−) carboxylic acid,
(d) reacting, if desired, the (+) or (−) acid from step (c) with oxalyl chloride to form the corresponding (+) or (−) acid chloride, and
(e) esterifying the (+) or (−) acid chloride from step (d) with ethanol and sodium to produce the desired (+) or (−) ethyl ester.

Alternatively the + or − acid chloride of step (d) is reacted with 2-(N-benzyl-N-methylamino)-ethanol to produce the corresponding (+) or (−) ester.

The instant invention further concerns a pharmaceutical composition for treating blood vessel diseases comprising an effective amount of one of the above compounds in admixture with a solid or liquid pharmaceutical diluent or carrier.

The instant invention further concerns a method for treating diseases of blood vessels which comprises treating a mammal suffering therefrom with the above pharmaceutical composition.

DETAILED DESCRIPTION

Both of the naphthyridine derivatives of formulae I and II above are active compounds and are chiral compounds. The weakly basic racemic compounds resulting in the case of the synthesis could hitherto not be separated directly into the enantiomeric forms with optically-active auxiliary compounds. The separation of the corresponding naphthyridine-3-carboxylic acid into the optical antipodes by fractional crystallization with optically-active bases has hitherto also not been possible. However, the separation of the compounds of formulae (I) and (II) into the optical antipodes is desired since, in pharmacological comparative experiments, it has been ascertained that the dextrorotary enantiomers are substantially more strongly effective than the racemates.

The present invention provides an economical process which can be carried out on a large scale for separating a synthesis intermediate or a derivative of these compounds into the enantiomers and then to convert these into the optically-active final compounds.

One possibility for the synthesis of the enantiomeric forms on a gram scale is via the diastereomeric 1-phenylethyl esters. However, the S-(−)-1-phenylethanol necessary for this purpose is very expensive. After separation of the dextrorotary diastereomers, the 1-phenylethyl ester is cleaved hydrogenolytically and the S-(−)-1-phenylethanol can no longer be used for further separations.

Surprisingly, it has now been found that the benzyl esters of these naphthyridine-3-carboxylic acids form with optically-active 0,0'-dibenzoyltartaric acid in various solvents, preferably in alcohols, readily crystallizing diastereoisomeric salts which can be separated by fractional crystallization. The chiral benzyl esters can then be easily converted with good yield either by transesterification directly into the desired esters or the benzyl esters can first be converted by catalytic hydrogenation into the carboxylic acids and these converted via the acid chloride and reaction thereof with the appropriate alcohol into the desired chiral end products. In both cases, no racemization takes place.

Therefore, the instant invention provides a novel process for separating the racemic benzyl ester (±)-1,4-dihydro-5-isopropoxy-2-methyl-4-(2-trifluoromethyl-phenyl)-1,6-naphthyridine-3-carboxylic acid benzyl ester, which is easy to prepare as an intermediate product, with the help of optically active (+)- or (−)-O,O'-dibenzoyltartaric acid (DBTA) via the fractional crystallization of the diastereoisomeric salts, into the dextrorotary and levorotary enantiomers. The (+) or (−)-O,O'-dibenzoyltartaric acid is used for this purpose for economical reasons. Furthermore, after the separation has taken place, the optically active dibenzoyltartaric acid can be recovered and used again.

According to the present invention, it is possible to prepare the desired enantiomerically-pure calcium antagonists in comparatively large amounts and in an economical form. The process results in a distinct saving due to the lower costs for the auxiliary reagents for the racemate separation and the auxiliary reagent O,O'-dibenzoyltartaric acid can, in contradistinction to 1-phenylethanol, even be used repeatedly. Furthermore, by the instant process saves at least three and possibly even five synthesis steps, as is illustrated in Scheme I below.

SCHEME I

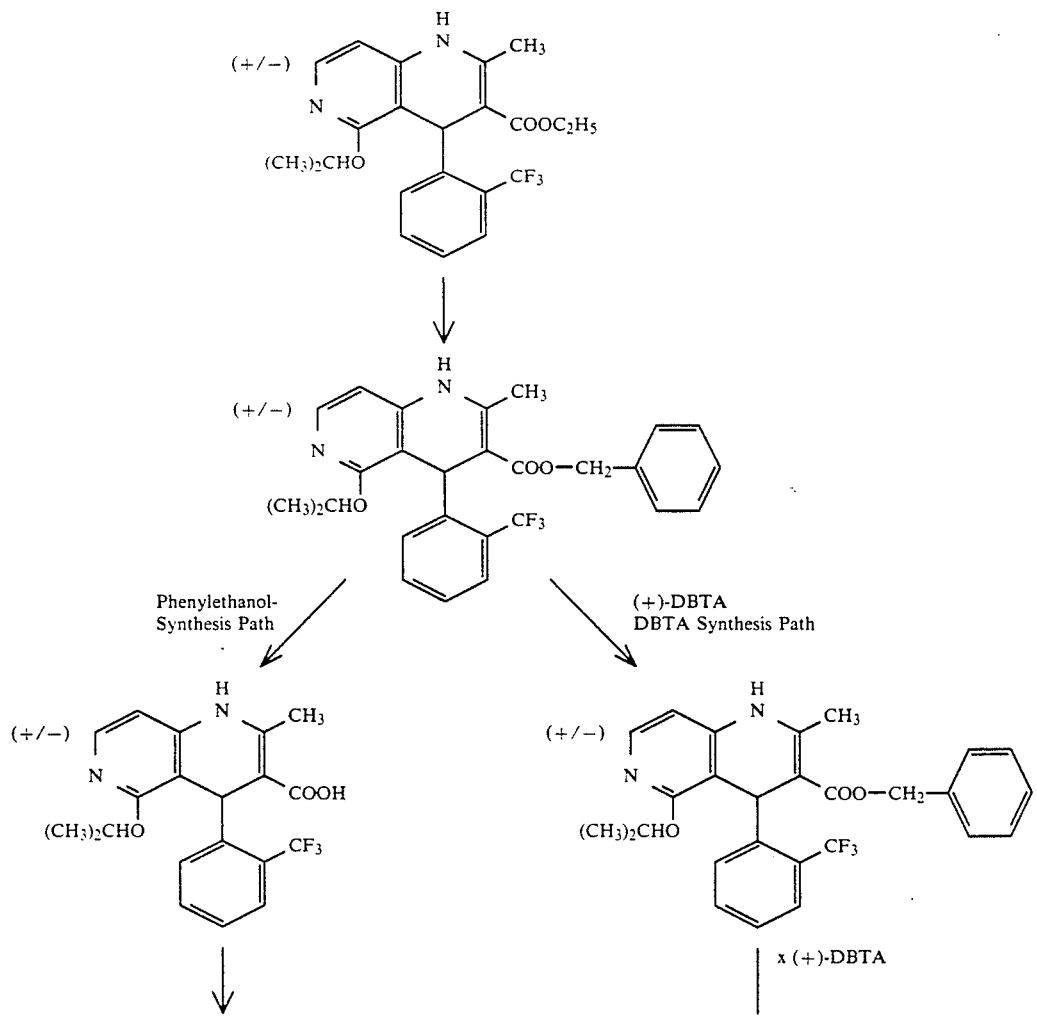

-continued
SCHEME I
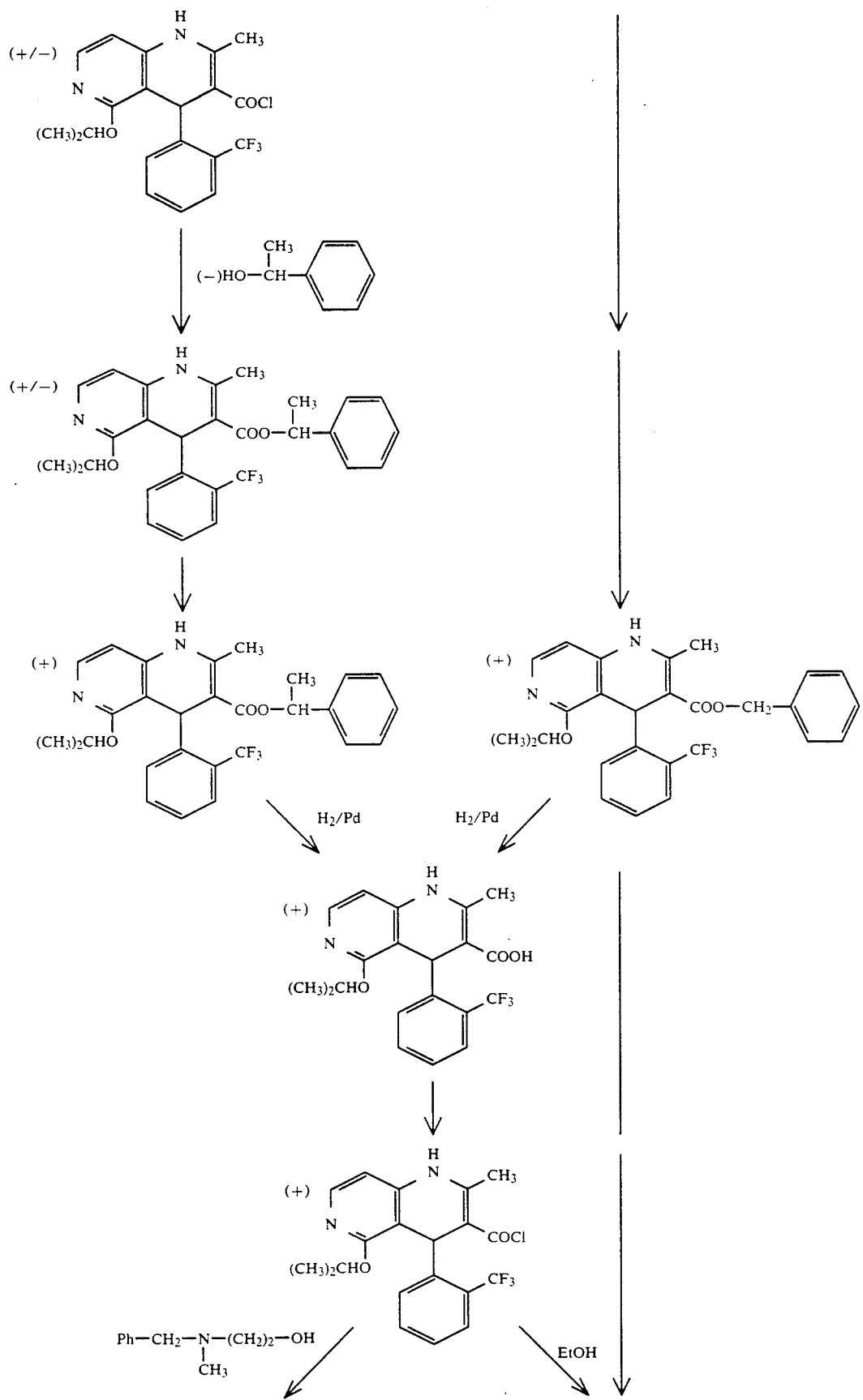

-continued
SCHEME I

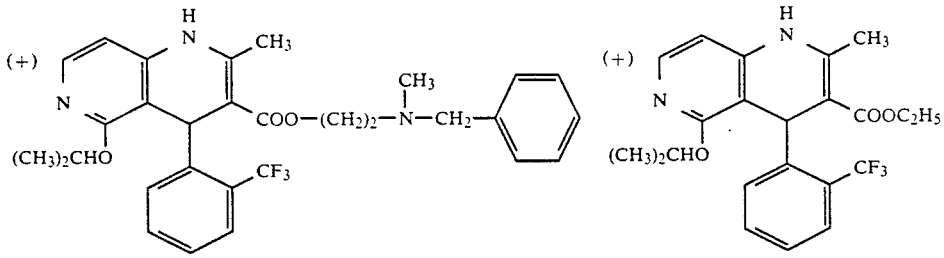

The compounds of the instant invention are highly effective calcium antagonists. As compared to known calcium antagonists, at therapeutic concentrations, a cardiodepression (negative inotropic, negative chronotropic action) is not to be expected.

On the basis of their blood vessel spasmolytic actions, they are especially indicated in the case of cerebral, cardial, and peripheral blood vessel diseases, such as myocardial ischemia, cerebral infarct, pulmonary infarct, pulmonary thromboses, and arteriosclerosis or other stenotic indications, especially because, in comparison with known compounds with a similar mode of action, negative inotropic side effects are substantially absent. Therefore, the 1,6-naphthyridine derivatives of the present invention are valuable agents for combatting heart-circulating mortality.

Consequently, a further subject of the present invention is the use of the instant 1,6-naphthyridine derivatives for combatting blood vessel diseases.

The compounds of the present invention can be administered orally or parenterally in liquid or solid form. As injection solution, water is preferably used which contains the additives usual in the case of injection solution, such as stabilizing agents, solubilizing agents or buffers.

Additives of this kind include, for example, tartrate and citrate buffers, ethanol, complex formers (such as ethylenediamine-tetraacetic acid and the nontoxic salts thereof), as well as high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, also contain flavoring and/or sweetening agents.

Individual dosages to be administered enterally are in the range of from about 5 to 250 mg and preferably from 20 to 100 mg. Parenterally, about 1 to 20 mg are administered.

The following examples are provided for the purpose of illustrating the present invention.

EXAMPLE 1

(±)-1,4-Dihydro-5-isopropoxy-2-methyl-4-(2-trifluoromethylphenyl)-1,6-naphthyridine-3-carboxylic acid benzyl ester In a 500-mL four-necked round-bottom flask equipped with a stirrer, dropping funnel, reflux condenser with gas lead-off, a thermometer and a gas inlet are placed 100 mL benzyl alcohol and 0.937 g (0.0312 mole) sodium hydride (80% in oil) is introduced while flushing with a protective gas. The resulting suspension is then subsequently stirred for 30 minutes. Thereafter, a solution of 52.55 g (0.124 mole) (±)-1,4-dihydro-5-isopropoxy-2-methyl-4-(2-trifluoromethylphenyl)-1,6-naphthyridine-3-carboxylic acid ethyl ester in 200 mL benzyl alcohol is allowed to run in, followed by stirring for 15 hours at 120° C. After cooling to ambient temperature, the reaction mixture is stirred with 1 L of water and 400 mL dichloromethane. After separating the phases, the aqueous phase is again stirred with 300 mL dichloromethane. The dichloromethane phases are combined and washed twice with 300 mL amounts of water. The dichloromethane phase is dried over anhydrous sodium sulfate. After filtering, the dichloromethane is distilled off on a rotary evaporator and subsequently the benzyl alcohol is distilled off under oil pump vacuum (54°–65° C./3–5 mm Hg). The distillation residue is dissolved in 600 mL hot cyclohexane and the solution is cooled to 0° C. while stirring. The precipitate obtained is filtered off with suction and subsequently washed with 100 mL n-hexane. The filter cake is then dried at 80° C. Yield: 43.9 g (72.8% of theory); mp 131° C. with a purity of 99.4 relative %.

EXAMPLE 2

(+)-1,4-Dihydro-5-isopropoxy-2-methyl-4-(2-trifluoromethylphenyl)-1,6-naphthyridine-3-carboxylic acid benzyl ester 1.93 g (0.004 mole) (±)-1,4-dihydro-5-isopropoxy-2-methyl-4-(2-trifluoromethylphenyl)-1,6-naphthyridine-3-carboxylic acid benzyl ester (Example 1) and 1.50 g (0.004 mole) (+)-0,0'-dibenzoyl-D-tartaric acid monohydrate are dissolved in 20.6 mL hot isopropyl alcohol. The solution is left to stand for several days at 8° C. The precipitated product is filtered off with suction and dried in a vacuum drying cabinet at 40° C. (Yield: 588 mg; mp 159°–162° C.; $[\alpha]_D = +82.6°$ (c=1/methanol)).

For the liberation of the base, the salt is suspended in 19 mL of 1N aqueous sodium hydroxide solution and extracted five times with 7 mL amounts of toluene. The combined organic phases are washed once with 7 mL 1N aqueous sodium hydroxide solution and three times with 7 mL of water. The organic phase is dried over anhydrous sodium sulfate and subsequently evaporated to dryness on a rotary evaporator. The solid residue is recrystallized from 20 mL n-hexane. The crystallizate obtained is dried in a vacuum drying cabinet at 40° C. (Yield: 300 mg (31.08% of theory); mp 110°–111° C.; $[\alpha]_D = +39.3°$ (c=1/dichloromethane)).

EXAMPLE 3

(−)-1,4-Dihydro-5-isopropoxy-2-methyl-4-(2-tri-fluoromethylphenyl)-1,6-naphthyridine-3-carboxylic acid benzyl ester 9.65 g (0.02 mole) (±)-1,4-dihydro-5-isopropoxy-2-methyl-4-(2-trifluoromethylphenyl)-1,6-naphthyridine-3-carboxylic acid benzyl ester (Example 1) and 15.04 g (0.04 mole) (−)-O,O'-dibenzoyl-L-tartaric acid monohydrate are dissolved in a hot mixture of 100 mL ethanol and 70 mL of water. The solution is allowed to cool slowly to 20° C. The precipitated product is filtered off with suction and dried in a vacuum drying cabinet at 40° C.

For the liberation of the base, the salt is suspended in 19 mL 1N aqueous sodium hydroxide solution and extracted five times with 7 mL amounts of toluene. The combined organic phases are washed once with 7 mL 1N aqueous sodium hydroxide solution and three times with 7 mL of water. The organic phase is dried over anhydrous sodium sulfate and subsequently evaporated to dryness on a rotary evaporator. The solid residue is recrystallized from 20 mL n-hexane. The crystallizate is dried at 40° C. in a vacuum drying cabinet; mp 110° C.; $[\alpha]_D = +39.3°$ (c=1/dichloromethane), yield 1.3 g=27.7%.

EXAMPLE 4

(+)-1,4-Dihydro-5-isopropoxy-2-methyl-4-(2-tri-fluoromethylphenyl)-1,6-naphthyridine-3-carboxylic acid 1.6 g (0.00331 mole) (+)-1,4-dihydro-5-isopropoxy-2-methyl-4-(2-trifluoromethylphenyl)-1,6-naphthyridine-3-carboxylic acid benzyl ester is taken up in 32 mL ethanol and hydrogenated without the use of pressure at 20° C. in the presence of 0.64 g 10% palladium/charcoal (50% moist). The catalyst is filtered off and the filtrate evaporated to dryness at 35° C. on a rotary evaporator. The solid residue is recrystallized from 10 mL diisopropyl ether. The product is dried at 40° C. in a vacuum drying cabinet; yield: 1.04 g (80.3% of theory).

EXAMPLE 5

(+)-1,4-Dihydro-5-isopropoxy-2-methyl-4-(2-tri-fluoromethylphenyl)-1,6-naphthyridine-3-carboxylic acid ethyl ester 31.4 mg oxalyl chloride are added to a solution of 0.5 mL anhydrous dimethylformamide in 3 mL anhydrous dioxan cooled to 3° C., followed by stirring for 40 minutes at 0° to 5° C. After adding 85 mg (+)-1,4-dihydro-5-isopropoxy-2-methyl-4-(2-trifluoromethylphenyl)-1,6-naphthyridine-3-carboxylic acid, dissolved in 1 mL anhydrous dioxan, the cooling is removed, followed by stirring for 2.5 hours. After adding 2 mL ethanol, the reaction mixture is first stirred for 2 hours at ambient temperature and thereafter for 30 minutes at 40° to 50° C. The reaction mixture is subsequently stirred with 30 mL 2N aqueous sodium carbonate solution and 10 mL dichloromethane. The organic phase is separated off and the aqueous phase subsequently extracted three times with 10 mL amounts of dichloromethane. The combined organic phases are dried over anhydrous sodium sulfate and then evaporated to dryness. The residue is purified over silica gel with n-hexane/ethyl acetate (1:1 v/v) as elution agent and subsequently recrystallized from n-hexane. Yield: 32 mg (38.5% of theory); mp 130° C.; $[\alpha]_D = +105°$ (c=0.5/dichloromethane).

EXAMPLE 6

(+)-1,4-Dihydro-5-isopropoxy-2-methyl-4-(2-tri-fluoromethylphenyl)-1,6-naphthyridine-3-carboxylic acid ethyl ester 1.44 g (+)-1,4-dihydro-5-isopropoxy-2-methyl-4-(2-trifluoromethylphenyl)-1,6-naphthyridine-3-carboxylic acid benzyl ester is introduced into a solution of 100 mg sodium in 90 mL anhydrous ethanol and boiled under reflux for 20 hours. The reaction mixture is evaporated, the residue is taken up in 50 mL dichloromethane and extracted three times with 20 mL amounts of water. The organic phase is dried over anhydrous sodium sulfate and thereafter evaporated to dryness. The residue is recrystallized from 20 mL n-hexane. The filter cake is dried to constant weight at 30° C. in a vacuum drying cabinet. Yield: 850 mg (67.38% of theory); mp 130° C.; $[\alpha]_D = +110°$ C. (c=0.5/dichloromethane).

EXAMPLE 7

(−)-1,4-Dihydro-5-isopropoxy-2-methyl-4-(2-tri-fluoromethylphenyl)-1,6-naphthyridine-3-carboxylic acid 17 g (0.0352 mole) (−)-1,4-dihydro-5-isopropoxy-2-methyl-4-(2-trifluoromethylphenyl)-1,6-naphthyridine-3-carboxylic acid benzyl ester is taken up in 340 mL ethanol and hydrogenated without the use of pressure at 20° C. in the presence of 6.8 g 10% palladium/charcoal (50% moist). The catalyst is filtered off and the filtrate evaporated to dryness at 35° C. on a rotary evaporator. Yield: 15.1 g (89.2% of theory).

EXAMPLE 8

(−)-1,4-dihydro-5-isopropoxy-2-methyl-4-(2-tri-fluoromethylphenyl)-1,6-naphthyridine-3-carboxylic acid [2-(N-methyl-N-phenylmethylamino)ethyl]ester 6.29 g oxalyl chloride in 73 mL ethyl acetate are added to a solution of 11.3 mL absolute dimethylformamide in 220 mL absolute ethyl acetate cooled to 0° C., followed by stirring for 15 minutes at 0° to 5° C. After adding of 12.8 g (−)-1,4-dihydro-5-isopropoxy-2-methyl-4-(2-trifluoromethylphenyl)-1,6-naphthyridine-3-carboxylic acid there are added dropwise 3.9 g pyridine, dissolved in 73 mL ethyl acetate and the mixture is stirred for 60 minutes at 0° C. After adding of 10.26 g 2-(N-benzyl-N-methylamino)-ethanol, dissolved in 3.03 g pyridine and 146 mL methylene chloride the mixture is stirred for 1 hour at 5° to 10° C. The reaction mixture is subsequently stirred with 3×140 mL water and 2×140 mL 1N sodium hydroxide. The organic phase is separated off, dried over sodium sulfate and evaporated to dryness. The oily residue is purified over silica gel with toluene:ethyl acetate (7:3) as elution agent. After distilling off the elution agent there is obtained an oily product. The oil is dissolved with 2.52 g fumaric acid in 350 mL ethyl acetate under heating to reflux temperature. After filtration the reaction mixture is evaporated to about 50 mL. The precipitated product is filtered off with suction, dispersed in 10 mL toluene and stirred with 5 mL 1M aqueous ammonium hydroxide solution. The toluene phase is washed with 2×5 mL of water. The organic phase is after drying over sodium sulfate evaporated to dryness. There is obtained an oily product, yield 5.3 g (32% of theory); $[\alpha]_D = -40.8°$ (c=1/dichloromethane).

EXAMPLE 9

(−)-1,4-dihydro-5-isopropoxy-2-methyl-4-(2-trifluoromethylphenyl)-1,6-naphthyridine-3-carboxylic acid [2-(N-methyl-N-phenylmethylamino)ethyl]ester To a solution of 21.05 g 2-(N-benzyl-N-methylamino)-ethanol in 42 mL toluene are added under nitrogen 0.74 g sodium hydride (80%). After stirring for 30 minites a solution of 8.42 g (0.0174 mole) (−)-1,4-dihydro-5-isopropoxy-2-methyl-4-(2-trifluoromethylphenyl)-1,6-naphthyridine-3-carboxylic acid benzyl ester is added dropwise. The reaction mixture is stirred under nitrogen and the exclusion of moisture for 4 hours by heating to boiling temperature under reflux. The reaction mixture is subsequently extracted with 2×50 mL 2N acetic acid. The reaction mixture is subsequently dried over sodium sulfate and evaporated to dryness. The residue is purified over silica gel with toluene:ethyl acetate (7:3) as elution agent. After distilling off the elution agent there is obtained an oily product. The oil is dissolved with 1.28 g fumaric acid in 180 mL ethyl acetate under heating to reflux temperature. After filtration the reaction mixture is evaporated to about 20 mL. The precipitated product is filtered off with suction, dispersed in 14 mL toluene and stirred with 3 mL 1M aqueous ammonium hydroxide solution. The toluene phase is washed with 2×5 mL of water. The organic phase is after drying over sodium sulfate evaporated to dryness. There is obtained an oily product, yield 0.8 g (8.5% of theory); $[\alpha]_D = -40.8°$ (c=1/dichloromethane).

EXAMPLE 10

(+)-1,4-dihydro-5-isopropoxy-2-methyl-4-(2-trifluoromethylphenyl)-1,6-naphthyridine-3-carboxylic acid [2-(N-methyl-N-phenylmethylamino)ethyl]ester 138 mg oxalyl chloride in 2 mL ethyl acetate are added to a solution of 248 mg absolute dimethylformamide in 4.1 mL absolute ethyl acetate cooled to 0° C., followed by stirring for 15 minutes at 0° to 5° C. After adding of 270 mg (+)-1,4-dihydro-5-isopropoxy-2-methyl-4-(2-trifluoromethylphenyl)-1,6-naphthyridine-3-carboxylic acid there are added dropwise 0.09 mL pyridine, dissolved in 2 mL ethyl acetate and the mixture is stirred for 60 minutes at 0° C. After adding of 224 mg 2-(N-benzyl-N-methylamino)-ethanol, dissolved in 4 mL methylene chloride the mixture is stirred for 1 hour at 5° to 10° C. The reaction mixture is subsequently stirred with 3×10 mL water and 2×10 mL 1N sodium hydroxide. The organic phase is separated off, dried over sodium sulfate and evaporated to dryness. The oil is dissolved with 78 mg fumaric acid in 5 mL ethyl acetate under heating to reflux temperature. After filtration the reaction mixture is evaporated to about 2 mL. The precipitated product is filtered off with suction, dispersed in 5 mL methylene chloride and stirred with 5 mL 1M aqueous ammonium hydroxide solution. The toluene phase is washed with 2×5 mL of water. The organic phase is after drying over sodium sulfate evaporated to dryness. There is obtained an oily product, yield 140 mg (38% of theory); $[\alpha]_D = +43.8°$ (c=1/dichloromethane).

We claim:

1. A process for the preparation of a compound selected from the group consisting of: (+)-1,4-dihydro-5-isopropoxy-2-methyl-4-(2-trifluoromethylphenyl)-1,6-naphthyridine-3-carboxylic acid ethyl ester, (−)-1,4-dihydro-5-isopropoxy-2-methyl-4-(2-trifluoromethylphenyl)-1,6-naphthyridine-3-carboxylic acid ethyl ester, (+)-1,4-dihydro-5-isopropoxy-2-methyl-4-(2-trifluoromethylphenyl)-1,6-naphthyridine-3-carboxylic acid, (−)-1,4-dihydro-5-isopropoxy-2-methyl-4-(2-trifluoromethylphenyl)-1,6-naphthyridine-3-carboxylic acid, (+)-1,4-dihydro-5-isopropoxy-2-methyl-4-(2-trifluoromethylphenyl)-1,6-naphthyridine-3-carboxylic acid[2-(N-methyl-N-phenylmethylamino)ethyl]ester, and (−)-1,4-dihydro-5-isopropoxy-2-methyl-4-(2-trifluoromethylphenyl)-1,6-naphthyridine-3-carboxylic acid[2-(N-methyl-N-phenylmethylamino)ethyl]ester which comprises:

(a) reacting (±)-1,4-dihydro-5-isopropoxy-2methyl-4-(2-trifluoromethylphenyl)-1,6-naphthyridine-3-carboxylic acid ethyl ester with benzyl alcohol to produce the corresponding (±) benzyl ester, (b) reacting the (±) benzyl ester from step (a) with (+) or (−) dibenzoyltartaric acid followed by fractional crystallization to produce the desired stereomeric salt, of the benzyl ester followed by converting said salt to the corresponding (+) or (−) benzyl ester, (c) hydrogenating the (+) or (−) benzyl ester from step (b) to produce the corresponding (+) or (−) carboxylic acid, (d) reacting, if desired, the (+) or (−) acid from step (c) with oxalyl chloride to form the corresponding (+) or (−) acid chloride, and (e) esterifying the (+) or (−) acid chloride from step (d) with ethanol or 2-(N-benzyl-N-methylamino) ethanol to produce the corresponding (+) or (−) ester.

* * * * *